United States Patent [19]

Pegel et al.

[11] 4,254,111

[45] Mar. 3, 1981

[54] STEROLIN PRODUCTS

[75] Inventors: Karl H. Pegel; Colin B. Rogers, both of Durban, South Africa

[73] Assignee: Roecar Holdings (Netherlands Antilles) NV, Amsterdam, Netherlands

[21] Appl. No.: 53,735

[22] Filed: Jul. 2, 1979

[30] Foreign Application Priority Data

Jul. 5, 1978 [GB] United Kingdom ............... 28833/78

[51] Int. Cl.$^3$ ...................... A61K 31/705; C07J 17/00
[52] U.S. Cl. .......................................... 424/182; 536/5
[58] Field of Search ............................. 536/5; 424/182

[56] References Cited

U.S. PATENT DOCUMENTS

| | | | |
|---|---|---|---|
| 3,944,660 | 3/1976 | Gottfried et al. ...................... | 424/44 |
| 3,963,697 | 6/1976 | Coombes .............................. | 424/182 |
| 3,991,186 | 11/1976 | Mural et al. ......................... | 424/182 |
| 4,021,535 | 5/1977 | Polito .................................. | 424/182 |
| 4,083,969 | 4/1978 | Inoue et al. .......................... | 424/182 |

OTHER PUBLICATIONS

Phillips, "Jour. of Steroid Biochemistry", vol. 6, 1975, pp. 607–613.
Windholz et al., "The Merck Index", 9th ed. Merck & Co., Inc. Rahway, N.J. 1976, p. 1795.

*Primary Examiner*—Johnnie R. Brown
*Attorney, Agent, or Firm*—Cushman, Darby & Cushman

[57] ABSTRACT

The invention is concerned with new chemical compounds being the hemiesters of steryl glycosides, methods of preparing these hemiesters, and pharmaceutically, particularly anti-inflammatory, compositions containing the new hemiesters.

18 Claims, No Drawings

STEROLIN PRODUCTS

This invention relates to dicarboxylic acid derived half esters of steryl glycosides and the salts of these compounds with respect to (1) their synthesis, (2) their incorporation into pharmaceutical and food products as well as (3) the use of these compounds and products. The medicinally useful properties of steryl glycosides (sterolins) and their esters (acyl sterolins) and their incorporation into pharmaceutical products have been described (1–10 and 47–52). It is suspected and in some instances known that the natural glycosides and glycoside esters of sterols are of biological importance in plants (11–13, 47 and 48), micro organisms (14–16), animals (1–10 and 47–52) and possibly also in insects (17). Steryl glycosides and their esters seem to be essential "vitamin-like substances" for mammals and other animals which cannot synthesize these compounds themselves, but obtain them through their diet primarily from plant sources. The use of steryl glycosides, especially glucosides, and their esters in medicinal and food products has been described in the patent literature (1–4 and 50–52) and reports on this topic have appeared in the scientific and medical literature (5–10, 18, 19), although the essential and important nature of sterolins do not seem to have been generally recognised (e.g. 9). Sterolins are probably involved in the control of cell growth and senescence in plants and they have found application in the treatment and prevention of diverse geriatric and civilisation diseases such as hypertrophy of the prostate, rheumatic and hyperlipidaemic manifestations (1, 3) and they are used as diuretics (5), in the treatment of hyperglycaemia (8, 10), as antiinflammatory agents (1, 3 and 49) and as haemostatic agents (52) etc. The parent sterols of the steryl glycosides described in this specification and the eight cited inventions (1–4 and 49–52) occur and are an absolute requirement in most living organisms (13, 20). Sterols are $C_{27}$, $C_{28}$ and $C_{29}$ compounds derived from the $C_{30}$ triterpene precursors lanosterol and cyclo-artenol through the loss of 3 skeletal methyl groups to give cholesteryl ($C_{27}$) which is the final end-sterol found in warm blooded animals and the various phytosterols in plants (11, 21) which usually carry 1 or 2 extra carbon atoms at C-24. The $C_{28}$ and $C_{29}$ phytosterols derived from cycloartenol occur in plants only and if found in warmblooded animals they have been derived from plant foods (22–25). Typical and common members of this group of phytosterols are sitosterol (the most common and abundant plant sterol formerly known as $\beta$-sitosterol, c.f. 12, 21 22), stigmasterol, campesterol, $\beta$-spinasterol and also cholesterol (15, 26); however, approximately 100 different phytosterols have been isolated, identified and described (21).

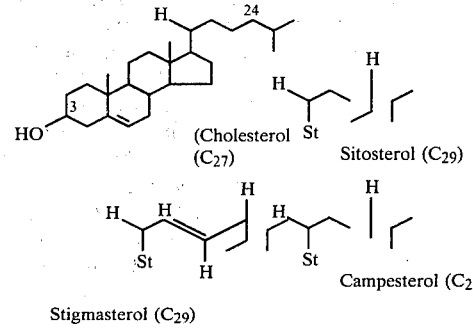

The $\beta$-3-sugar moiety of the steryl glycosides (sterolins) described in this specification consists usually and preferentially of one monosaccharide unit only, the most common one being glucose (12, 27 and 48), although mannose (12, 28), galactose (27, 29, 30), arabinose (31, 32), xylose (33) fructose (34) and glucuronic acid (35) and others (53) have been reported in naturally occurring sterolins. The glycoside link to the sterol 3-position is in most cases a $\beta$-glycoside. The synthetic possibilities are only limited by the number of available monosaccharides. Reports of disaccharide units are rare for either natural (36, 37) or synthetic (38, 39) sterolins and to our knowledge no trisaccharide or larger oligosaccharide units have been incorporated or found by others in natural (but see 27) or synthetic sterolins. We have found that sterolins with di-(2) and trisaccharide units show pharmacological properties similar to sitosteryl $\beta$-D-glucoside. However, it is known that although increased water solubility or at least hydrophilicity is achieved on enlarging the sugar moiety from a monosaccharide to di-, tri-, tetra- etc. oligosaccharides (39–41) there exists evidence that the biological activity of steroidal oligosaccharides seems to decrease as the monomer units in the carbohydrate moiety increase (42, but also see 41).

The common steryl monglycosides are virtually water insoluble (4, 19, 38, Table), but an increase in sterolin water solubility has been found for disaccharides (38 and also see 39) and trisaccharides as shown in the TABLE. The water insolubility of the monosaccharide sterolins is probably due to the strong intermolecular forces in their crystalline and amorphous aggregates, but these cohesive forces can be overcome by preparing monomolecular dispersions of the steryl glycosides with or in other substances thereby increasing the biological or pharmacological effect of such sterolin products (2, 43). Esterification of sterolins with monocarboxylic acids reduces their water solubility even more making them more lipophilic. In plants 6-O-acyl steryl $\beta$-D-glucosides of fatty acids are ubiquitous (12 and 48) and biological and pharmacological importance has been claimed for these natural mono- and synthetic peracylated sterolins (1, 3, 4 48, 49 and 52).

It is primarily for the purpose of providing water solubility to the steryl monosaccharides that the compounds of this invention, the dicarboxylic acid half ester derivatives and their salts, were prepared. No side effects have been observed on oral administration at normal or high dose levels, but toxic and other side effects have been noted on parenteral administration. In the TABLE the approximate water solubilities of a number of sterolins are compared with the solubilities of the corresponding sterolin hemisuccinates and their sodium salts as well as the solubilities of sterolin hemiesters and their salts of a few other selected dicarboxylic acids.

The increase in water solubility of the dicarboxylic acid sterolin hemiesters and their salts coupled with the unexpected enhanced biological effect of these derivatives forms the basis of this invention. If we consider sitosteryl β-D-glucoside then its four hydroxyl groups can give rise to a variety of different esterification products, namely mono-, di-, tri- and tetra esters. Amongst these there are four different possible monoesters, six diesters, four triesters, but only one tetraester if only one dicarboxylic acid (or monocarboxylic acid) is used. Also, when aiming at the formation of the sterolin diester, not only are the various diester isomers formed during the synthesis, but in addition some mono-, tri- and tetraesters will be produced, it is only possible to obtain a specific sterolin diester if special precautions involving complicated and often difficult reaction procedures are observed. In most instances the products of this invention are therefore mixtures of isomers and reaction cogeners averaging an ideal mean.

The application of the compounds of this invention in medicine, veterinary science and in the food industry is the same as described for sterolins above and sitosteryl β-D-glucoside and other related steryl glycosides (1, 3 and 52). However, whereas the steryl glycosides have to be dispersed monomolecularly in order to achieve maximum effect of the administered product or drug, the compounds of this invention do not require this high degree of separation. Nevertheless, for practical purposes the sterolin dicarboxylic acid hemiesters or their salts have to be mixed with additives such as pharmaceutically acceptable carriers, diluents, dispersants, and the like and if required, other pharmaceutically active agents may be incorporated or added in the manufacture of the final product. Alternatively the products of the invention may be added to or mixed into foodstuffs for human and animal consumption. Ideally these sterolin hemidicarboxylate acid esters or their salts should be incorporated into dry, solid pharmaceutical or food products, but oil or other non aqueous solvent preparations can also be used. It is advisable to avoid the incorporation of these products in mixtures containing water since this will result in the slow hydrolytic decomposition of the ester bond thereby generating the free insoluble sterolin. However, it must be remembered that in such an event the resulting free sterolin will probably exist in a monomolecularly dispersed form in which it is readily available for assimilation.

Preferred daily doses of the compounds of this invention depend on the purpose for which they are used, administered or applied and also whether they are given by oral or parenteral routes or applied topically. Some of the compounds produce haemolysis of erythrocytes in vitro and may exhibit dermo-necrotic actions when administered parenterally (e.g. subcutaneously). They may be toxic when administered in large amounts and therefore the oral route is preferred. In the case of sitosteryl or cholesteryl monoglucoside dihemisuccinates no toxic effects have been observed during acute toxicity studies in rats and primates following the oral administration of large amounts even in excess of 1000–2000 mg/kg. Doses of 100–200 mg/kg bodyweight given daily over prolonged periods of time are well tolerated by these species. In human pilot studies, doses of 200 mg per day have also been well tolerated without observable adverse reactions. If taken for prophylactic purposes by healthy individuals a daily dose of 0.01–0.1 mg is adequate, although this may be raised to 0.2–1 mg for elderly people. Depending on the severity of a degenerative disease daily doses of 0.3–44 mg may be used for initial treatment until on improvement of the particular condition, a maintenance dose of 0.03–0.6 mg per day is advisable. Lower daily doses are required when these compounds are administered parenterally (e.g. via an intravenous drip). It should be noted that with respect to animals a preferred dose is difficult to predict since it is known that marked differences exist between species and even various breeds or strains of animals in their ability to utilise or react to steroidal glycosides (44–46).

The compounds of the invention can according to our present invention be used in the treatment of a number of diseases—see Example 5, pages 18–20.

EXAMPLE 1.

The standard preparation of the dicarboxylic acid half esters of sterolins illustrated by the synthesis of sitosteryl β-D-glucoside dihemisuccinate.

A solution of succinic anhydride (8.6 g, 0.086 mole) and anhydrous sitosteryl β-D-glucoside (24.7 g, 0.043 mole) in anhydrous pyridine (90 ml) was refluxed for 30 minutes and then left to stand for 20 hrs before it was poured into vigorously stirred conc. hydrochloric acid (104 ml) at ice temperature. The mixture was allowed to stand for 2 hrs before the precipitated hemiester was gravity filtered. The collected solid, washed with iced water until the washings were neutral, was dried in a vacuum oven and a small sample of this was dried to constant weight for a C and H analysis. The sitosteryl β-D-glucoside dihemisuccinate (31.5 g, 94% yield) so obtained had the following characteristics: m.p. 246° C. (gradual softening with slight decomposition, i.e. browning, with a clear melt reached at the given temperature), (Found: C, 65.2; H, 9.2. $C_{43}H_{68}O_{12}$ requires C, 66.5; H, 8.8%; mol. mass, 776); solubility in g per l water at 25° C: $5 \times 10^2$ g form a white gel, gradually becoming colloidal on dilution to $1.25 \times 10$ g.

Note 1—The TABLE annexed hereto records the m.p., formula and molecular mass, microanalytical C and H values as well as the reagent ratios used for some of the compounds or products prepared together with the data for some of their salts and the parent sterolins. In addition the TABLE records the solubilities of some of the compounds listed.

Note 2—The (a) sterols, (b) sugars and (c) dibasic acids used to prepare some of the compounds described in this specification are the following:
  (a) sitosterol, stigmasterol, cholesterol, cholestanol, ergosterol, lanosterol and 22, 23-dihydrolanosterol;
  (b) glucose, galactose, maltose, lactose, cellobiose and 6-glucosyl β-D-maltoside;
  (c) succinic acid, glutaric acid, maleic acid, cyclohexan-1,2-dicarboxylic acid and phthalic acid.

These compounds serve as examples within their group without limiting the scope of the claims. All sterols, carbohydrates and dibasic acids as described in the specification are included and can be incorporated into the compounds and products of this invention, provided they are pharmaceutically acceptable.

Note 3—With respect to the monosaccharide sterolins and the easily and economically prepared hemisuccinates, the dihemisuccinates and their salts are the preferred compounds and products of this invention. While the monohemisuccinates and their sodium salts are still relatively water insoluble the corresponding dihemisuccinate solubility or hydrophilicity is approximately 25 times as high. Also, in animal tests fewer adverse effects coupled with a lower tissue toxicity were observed on intraperitoneal administration of the sodium salt of sitosteryl β-D-glucoside dihemisuccinate than when the more soluble tri- and tetra-hemisuccinates sodium salts were administered. In addition the succinates are preferred to all of the other quoted hemiesters because succinic acid belongs to the Kreb's citric acid cycle group of compounds.

Note 4—The method described for the preparation of sitosteryl β-D-glucoside dihemisuccinate can be easily modified by altering the molar reagent proportions in order to prepare the mono-, tri- and tetra-hemisuccinates. Similarly the hemiesters of other dibasic esters may be prepared. Adjustment may be required:

(a) solvent volumes may have to be altered or the solvent may even be changed by using piperidine, dimethylformamide etc.;

(b) reaction conditions may have to be altered in that refluxing conditions are required and so on. Alternatively the compounds of this invention may be prepared by chemical methods other than those described in this specification and its examples which are to be regarded as non-limiting examples only.

EXAMPLE 2.

The standard preparation of the sterolin dicarboxylic acid hemiester salts illustrated by the preparation of the disodium salt of sitosteryl β-D-glucoside dihemisuccinate. The wet sitosteryl β-D-glucoside dihemisuccinate washed clear of hydrochloric acid as described in Example 1 was transferred quantitatively into a sodium bicarbonate solution (200 ml water; 7.2 g or 0.086 mole $NaHCO_3$). This mixture cooled to 0° C. was slowly poured with vigorous stirring into ice cold acetone (2000 ml) and the white precipitate of the salt was allowed to settle over 18 hrs in an ice chest before it was filtered under suction. The moist salt was thoroughly stirred into ice cold acetone (200 ml), the slurry suction filtered and the filter cake washed with cold ether before the product was dried in a vacuum oven at 40° C. for 48 hrs followed by 2×1 minute heating in a microoven. The white granular disodium salt of sitosteryl β-D-glucoside dihemisuccinate ground to a white powder had the following characteristics: m.p. 320° C. (slow softening with decomposition, i.e. browning with a clear melt reached at the given temperature), (Found C, 62.2; H, 8.0. $C_{43}H_{66}O_{12}Na_2$ requires C, 62.9; H, 8.0%; mol. mass (820); solubility in g per 1 water at 25° C: $5 \times 10^2$ g form a thick syrup thinning on dilution to $2 \times 10$ g to an almost clear solution.

Note 1—see Note 1 in example 1
Note 2—see Note 2 in example 1
Note 3—see Note 3 in example 1
Note 4—The preparation of the sodium salts and acid sodium salts of other sterolin hemisuccinate esters or hemidicarboxylic acid esters follows similar procedures as those described in example 2 except that adjustments in molar ratios of the reagents and solvent volume etc. have to be made. Alternatively the salts of the compounds or products of this invention may be prepared by other chemical methods available to the expert.

Note 5—Cations other than sodium may be introduced to produce for example the K, $NH_4$, Mg, Ca etc. salts including amine salts and provided that the cation is biologically or pharmaceutically acceptable.

EXAMPLE 3.

The preparation of pharmaceutical products incorporating the compounds of the invention (a) The disodium salt of sitosteryl β-D-glucoside dihemisuccinate (2.1 mg) is dissolved in warm water (500 ml, approx. 60° C.) to give a colloidal sol which is stirred into a slurry of talc (1000 g) in water (1 liter) at room temperature. The mixture is dried under reduced pressure at 60° C. with stirring and the dry product is repowdered before it is filled into capsules each carrying approximately 100 mg and hence 0.21 mg sitosteryl glucoside dihemisuccinate disodium salt ($Na_2SGDS$).

(b) Disodium sitosteryl β-D-glucoside dihemisuccinate salt (21 g), saffron (100 mg) and anhydrous glucose (5 g) are mixed (in a pestle or mortar or by any other mechanical means) until an even coloured product is obtained. This process is repeated 5 times approximately doubling the added amount of glucose (5, 10, 35, 100, 300 g) giving a total of 450 g primary product which is then thoroughly mixed with 9.55 kg anhydrous glucose. This final mixture is filled into capsules each carrying approximately 100 mg and hence 0.21 mg sitosteryl glucoside dihemisuccinate disodium salt ($Na_2SGDS$).

Note 1. The product described under (a) and (b) above are useful in the treatment of benign hypertrophy of the prostate where a patient is given 1 unit dose containing 0.21 mg $Na_2SGDS$ three times a day.

Note 2. The amount of $Na_2SGDS$ per unit dose can be altered depending on its intended use which may be for therapeutic, maintenance or prophylactic purposes.

Note 3. Any of the compounds of the invention may be incorporated into the final product and the carrier or diluent material may be any single pharmaceutically acceptable substance or a mixture of two or more such substances. In addition the final product may incorporate other pharmaceutically active compounds such as ascorbic acid, acetyl salicylic acid, paracetamol and the like which have an activity effect entirely on their own or they may interact synergistically with the compounds of this invention.

Note 4. The final product incorporating the compounds of this invention may be filled into capsules as described, but alternatively they may be pressed into pills or capsules or even distributed in powder form. In addition the compounds of the invention may be incorporated into solutions, emulsions or suspensions.

Note 5. The incorporation of the compounds of the invention into pharmaceuticals (medicinal and veterinary) has been described, but their incorporation or addition to any type of foodstuff, solid or liquid, for human and animal consumption is included.

EXAMPLE 4.

The anti-inflammatory effects of the disodium salt of sitosteryl β-D-glucoside dihemisuccinate ($Na_2SGDS$):

(a) ORAL ADMINISTRATION OF $Na_2SGDS$:

Twenty male Sprague-Dawley rats, (original supplier: Blue Spruce; Altamont U.S.A.) weighing 240-260 g, were acclimatized for at least 10 days to the test environment.

The test substance was suspended in a 1% m/v Tylose ® solution made up with distilled water. The selected test doses of the compounds were administered by force feeding at the rate of 1.0 ml/100 g body weight 24.0 hrs and 1.0 hour before the intra-plantar administration of the phlogegenic agent. Brewer's Yeast served as the inflammation-inducing substance and was injected at the rate of 0.1 ml of a 2% suspension made up in sterile saline into the right hind paw. (The left hind paw was injected with 0.1 ml saline only and served as the control foot.)

Ten animals were killed 5 hours after the challenge in order to determine the effect of the test substance on the accute inflammatory process. The remaining members of the group were sacrificed after 24 hours and used to assess the effect of the test compound on the secondary, residual inflammatory action of yeast. The average amount of oedema and swelling produced in the right foot by yeast was obtained by subtracting the weight of the foot from the weight obtained of the control (saline) side. The results obtained from the treated groups were compared to the relevant control groups which received a similar volume of the aqueous Tylose ®-solution only and the difference was expressed as a percentage increase or decrease over the control value.

The average reduction in inflammation is exhibited in the following TABLE:

| DOSE × mg/kg | AVERAGE PERCENTAGE REDUCTION OF RAT PAW-OEDEMA / INFLAMMATION | |
|---|---|---|
| | after 5 hours | after 24 hours |
| 500 | 8,5 | 10,7 |
| 1000 | 14,5 | 18,5 |

× The dose was administered 24,0 hours and 1,0 hour before challenge with yeast.

Other compounds of the invention and their precurser sterolins were investigated under similar conditions.

(b) INTRAPERITONEAL ADMINISTRATION OF Na$_2$SGDS:

Groups of 20 male Sprague-Dawley rats, weighing 250 (±10 g) were acclimatized to the test environment. The test compound was made up in physiological saline at concentrations allowing the selected dose to be administered intraperitoneally at the rate of 0.1 ml/100 g body weight.

The test agent was administered 1.0 hour before the challenge with Brewer's Yeast. Otherwise the test procedure described under (a) was followed. The data obtained are presented in the following TABLE:

| DOSE × mg/kg | AVERAGE PERCENTAGE REDUCTION OF RAT PAW-OEDEMA / INFLAMMATION | |
|---|---|---|
| | after 5 hours | after 24 hours |
| 25 | 27 | 14 |
| 50 | 47 | 35 |

× A single dose was administered intraperitoneally 1 hour before the challenge with yeast.

Other compounds of the invention and their precursor sterolins were investigated under similar conditions. Some of the results are presented in the collectively below in TABLE 2.

(c) TOXICITY TRIAL AFTER ADMINISTRATION OF A SINGLE PARENTERAL OR ORAL DOSE OF THE COMPOUNDS OF THIS INVENTION:

Male rats of Sprague-Dawley strain and with a weight of 250-350 g were injected intraperitoneally with 0.1-0.5 ml/100 g body weight of an aqueous solution or suspension. Oral administration was carried out as described under (a). Examination of the acute toxicity was carried out after 7 days. The results are shown in the following TABLE 2.

TABLE 2

| ABREVIATIONS (used in TABLE) | |
|---|---|
| Beta-D-Glucoside | = BDGLU |
| Beta-D-Galactoside | = BDGAL |
| Beta-D-Maltoside | = BDMAL |
| Dihemiglutarate | = DHG |
| Dihemimaleate | = DHM |
| Dihemiphthalate | = DHP |
| Monohemisuccinate | = MHS |
| Dihemisuccinate | = DHS |
| Trihemisuccinate | = TRHS |
| Tetrahemisuccinate | = TEHS |
| Dihemicyclohexanedicarboxylate | = DHCYCLO |

| Substance | Reduction of the inflammatory response in the rat-paw oedema trials in % (bracketed numbers give the dose used in mg/kg body weight). | | Acute toxicity after a single dose | |
|---|---|---|---|---|
| | Oral mg/kg | Intraperitoneal mg/kg | Oral mg/kg | Intraperitoneal mg/kg |
| Sitosteryl-BDGLU-MHS | | −23.8 (50) | >1000 | |
| Sitosteryl-DHS | −37.2 (50) | −22.8 (50) | >1000 | from 75 to 150 mg = LD. 50 eg 100 = 25% |
| Sitosteryl-TRHS | | −52.4 (50) | >1000 | |
| Sitosteryl-TEHS | | −46.3 (50) | >1000 | 200 = 100% 100 = 20% |
| Sitosteryl-BDGAL-DHS | −74.9 (50) | −28.8 (25) | >1000 | 100 = 80% 50 = 66% 25 = 0% |
| Sitosteryl-BDGLU-DHG | | −44.6 (50) | >1000 | 125 = 50% 100 = 25% 62.5 = 0% |
| Sitosteryl-BDGLU-DHM | | −31.2 (50) | >1000 | 400 = 0% |
| Sitosteryl-BDGLU-DHCYCLO | | −61.6 (50) | >1000 | 125 = 100% 62.5 = 25% 50 = 0% |
| Sitosteryl-BDGLU-DHP | | −67.7 (50) | >1000 | 125 = 100% 100 = 40% 75 = 25% |

EXAMPLE 5

Medicinal applications of the compounds and products of this invention: In the treatment and control of the disease conditions and for the purposes described below;

A. Alimentary tract and metabolism
  a. The addition, incorporation and/or enrichment of sterolins in any food, pharmaceutical or other product for human, veterinary or agricultural purposes;
  b. ulcers;
  c. normalisation of liver function;
  d. normalisation of appetite and weight;
  e. as ingredients for tonic type preparations to promote general well-being and health;
  f. treatment of geriatric complaints;

g. treatment of diabetes;
h. laxative.
B. Systemic hormonal conditions including the genitourinary system.
   a. The treatment of endocrine irregularities;
   b. diseases of the urinary tract;
   c. benign hypertrophy of the prostate gland and associated conditions caused by it;
C. Blood and blood forming organs.
   a. Hyperlipidemia and its reversible effects.
D. Cardiovascular system.
   a. Heart diseases and blood pressure;
   b. as a diuretic;
   c. as a preventative of and treatment for varicose veins, haemorrhoids and vessel diseases.
E. Dermatologicals.
   a. Dermatitis including eczema, acne and related conditions
   b. emollients and protectives.
F. Musculo-skeletal system.
   a. As an anti-inflammatory agent;
   b. rheumatic diseases in general;
G. Central nervous system.
   a. epilepsy.
H. Respiratory system.
   a. Allergies in general including asthma.
I. Various.
   a. As palliative and synergistic agents with other pharmaceuticals;
   b. as prophylactic agents to prevent or alleviate adverse effects and reaction caused by radiation, cytostatics and other pharmaceuticals;
   c. healing processes in general and in particular post- and preoperative treatment;
   d. to promote the healing and acceptance processes in organ transplant operations.

References.
1. (a) British Pat. No. 1,298,047 to R. W. Liebenberg: Therapeutic agents.
   (b) K. H. Pegel; Offenlegungsschrift No. 2113215: Therapeutisches Kompositum.
2. (a) K. H. Pegel; British Pat. No. 1,365,661: Improvement in or relating to the preparation of medicinal and food compositions.
   (b) K. H. Pegel; Offenlegungsschrift No. 2303247: Verfahren zur Herstellung von Stoffgemischen für Medizinische oder Nahrungsmittelzwecke.
3. (a) K. H. Pegel; British Pat. No. 1,417,272: Extraction of sterolins from plant material.
   (b) K. H. Pegel; U.S. Pat. No. 3,933,789: Extraction of sterolins from plant material.
   (c) K. H, Pegel; Offenlegungsschrift 2312285: Verfahren zur Herstellung von Sterolin reichen Produkten
4. M. Kawamata, H. Ushimaru, A. Sano, and Y. Takahashi; Offenlegungsschrift No. 2458890: Verfahren zur Herstellung wäaariger Lösungen von Steringlykosiden und ihrer Esterderivate.
5. K. Kar, J. P. S. Sarin, and N. M. Khanna, and Indian J. Pharmacy, 1977, 39, 17–18: Diuretic activity of oittadiuoside- a sterol glucoside from Vittadinia Australis A. Rich.
6. F. M. Hammouda, A. M. Rizh, H. Ghaltez, and MM M. M. Adbel-Gawad; Planta Medica, 1972, 22, 188–195 Chemical and pharmacological studies of Asphodelus microcarpus.
7. T. Namba, M. Yoshizaki, T. Tomimori, K. Kobashi, K. Mitsui, and J. Hase; Planta Medica, 1974, 25, 28–38: Fundamental studies on the evaluation of the crude drugs. I. Hemolytic and its protective activity of Ginseng Saponins.
8. S. H. Ambike, and M. R. R. Rao; Indian J. Pharm, 1967, 29, 91–94: Studies on a phytosterolin from the bark of Ficus reliogosa.
9. I. Bartov, P. Budowski and S. Bornstein, Poultry Sci., 1970, 49, 1501–1506: Anticholesterolic effects of unsaponifiable fractions of vegetable oils in chicks.
10. A. A. Olaniyi; Lloydia, 1975, 38, 361–362: A neutral constituent of Momordica foetida.
11. W. R. Nes; Lipids, 1974, 9, 596–612: Roll of sterols in membranes.
12. C. Grunwald; Ann. Rev. Plant Physiol., 1975, 26, 209–236: Plant sterol
13. G. A. Bean; Adv. Lipid Res., 1973, 11, 193–218: Phytosterols.
14. T. W. Esders and R. J. Light; J. Biol. Chem., 1972, 247, 7494–7497: Occurence of uridine diphosphate glucose: sterol glucosyl treansgerase Candida bogoriensis.
15. V. C. Dewey and G. W. Kidder; Biochem. Pharmacol., 1962, 11, 53–56: Biological activity of steryl glycosides.
16. P. F. Smith; J. Bacteriol., 1971, 108, 986–991: Biosynthesis of cholesteryl glucoside by Mycoplasma gallinarum.
17. M. Goto, M. Kamada, S. Imai, T. Murata, S. Fujioka, E. Fujita and Y. Hamura,; Chem. Abstr., 1966, 64, 7045 c: Mulberry and related materials.
18. R. M. Ma and P. S. Schaffer; Arch. Biochem. Biophys., 1953, 47, 419–423 B-sitosteryl D-glucoside and B-sitosterol from commercially dried grape fruit pulp.
19. L. Swell, E. Stutzmann, M. D. Law and C. R. Treadwell; Arch. Biochem. Biophys., 1962, 97, 383–386: Intestinal absorption of cholesterol-4-$C^{14}$-D-glucoside
20. W. Eichenber, Chimia, 1975, 29, 132–133: Uber den Steringehalt pflanzlicher Mikrosomen.
21. L. J. Goad and T. W. Goodwin, Progr. Phytochem., 1972, 3, 113–198: The biosynthesis of plant sterols.
22. E. Heftmann; Lipids, 1974, 9, 626–639: Recent progress in the biochemistry of plant steroids other than sterols.
23. W. A. Nes, J. W. Cannon, N. S. Thampi and P. A. Govinda Malya,; J. Biol. Chem., 1973, 248, 484–487, Lack of Mammalian reduction or alkylation of 24-methylene cholesterol.
24. M. T. R. Subbiah; Amer. J. Clin. Nutr., 1973, 26, 219–225: Dietary plant sterols—current status in human and animal sterol metabolism.
25. A. Weizel, Medz. Klinik, 1975, 70, 242–246: Beinflussung des Cholesterinstoffwechsels durch beta-Sitosterin.
26. T. Tsukamoto, A. Yagi, K. Mihashi and Y. Mori; Chem. Pharm. Bull., 1968, 16, 2123–2129: Studies on the plant sterols and triterpenes. III. Examination of non-glycosidal sterols and triterpenes in crude drugs.
27. S. S. Radwan, F. Spencer and H. L. Mangold; Chem. Phys. Lipids, 1975, 14, 72–80: Lipids in plant tissue cultures. IV. The characteristic patterns of lipid classes in callus cultures and suspension cultures.
28. W. Eichenberger and W. Menke; Z. Naturforsch., 1966 21b, 859–867: Sterole in Blättern und Chloroplasten.
29. G. Willuhn and J. Köstens; Phytochemistry, 1975, 14, 2055–2058: Die quantitative Verteilung der Sterine und Sterinderivate in Organen von Solanum dulcamara.

30. A. M. Osman, M. El-Garby Younes and A. Mokhtar; Phystochemistry, 1975, 14, 829–830: Sitosterol B-D-galactoside from Hibiscus sbdariffa.

31. H. K. Kim, N. R. Farnsworth, H. H. S. Fong, R. N. Blomster and G. J. Persinos; Lloydia, 1970, 33, 30–35: Isolation and identification of a tumor inhibitor from Wallenia yungensis (Mysinaceae) as mysine saponin.

32. D. S. Bhakuni, M. Mayer, K. A. Poyser, P. G. Sammes and M. Silva; Rev. Latinamer. Quim., 1973, 4, 166–170: Anticancer agents from Chilean plants. Maytenus boarica.

33. M. Tin-Wa, N. R. Farnsworth, H. H. S. Fong, R. N. Blomster, J. Trojanek, D. J. Abraham, G. J. Persinos, and O. B. Dokosi; Lloydia, 1971, 34, 79–87: Antitumor activity of Maytenus Senegalensis (Celastraceae) and a preliminary investigation.

34. H. S. Garg and C. R. Mitra; Planta Medica, 1967, 15, 74–80: Blighia sapida. I. Constituents of the fresh fruit.

35. J. Vrkoc; Coll. Czech. Chem. Comm., 1962, 27, 1345–1346: Plant Substances. 14. B-sitosteryl glucuronide.

36. I. Khanna, R. Seshadri, and T. R. Seshadri; Phytochemistry, 1974, 13, 199–202: Sterol and lipid components of green Thea sinensts.

37. S. A. I. Rizvi and O. C. Saxena; Arzneimittel Forschg. 1974, 24, 285–287: New glycosides, terpenoids, colouring matters, sugar and fatty compounds from the flowers of Salmalia malabarica.

38. Pl. A. Plattner and A. Uffer, Helu, Chim. Acta, 1945, 28, 1049–1053: Uber einige neue Glucoside der Steroid-Reihe.

39. Ch. Meystre and K. Miescher; Helv. Chim. Acta, 1944, 27, 231–236: Zur Darstellung von Saccharidderivaten der Steroide.

40. K. Meischer and Ch. Meystre; Helv. Chim. Acta, 1943, 26, 224–223: Uber Saccharide des Desoxy-cortico-steroids.

41. G. Wulff; Deutsch. Apoth.-Ztg., 1968, 108, 797–808: Neuere Entwickelungen auf dem Saponingebiet.

42. K. O. Haustein, R. J. Meggers and J. Hauptmann, Pharmacology, 1973, 10, 65–75: Structure-activity relationship of natural and semi-synthetic genins and glycosides as investigated on the smooth muscle of the guinea-pig ileum.

43. H. Rupprecht, G. Kindl and M. J. Biesack; Pharmazie, 1974, 29, 207–208: Sorptionsverhalten von Steroiden an Kieselsäureoberflächen.

44. T. Tobin, R. Henderson and A. K. Sen; Biochem, Biophys, Acta., 1972, 274, 551–555: Species and tissue differences in the rate of dissociation of oubain from (na+ +K+)-ATPase.

45. E. Erdmann and W. Schoner; Klin. Wschr., 1974, 52, 705–718: Eigenschaften des Receptors für Herzplycoside 46. L. Kofler and L. Lazair; Wiener Klinische Wschr., 1927, 16–18: Über die Resistenz dez Blutes verschiedener Tiere gegen Saponin- amolyse.

47. (a) Y. Kimura, A. Tietz and S. Tamara; Planta, 1975, 126, 289–292: Stigmasteryl-B-D-glucoside as an auxin synergist.
(b) A. Tietz, Y. Kimura, and S. Tamura; Z. Pflanzen physiol., 1977, 81, 57–67: Steryl-glucosides—a group of substances in plants with hormone-like activity and biphase dose response curve.

48. W. Eichenberger; Lipids and Lipid polymers in the Higher Plant (Pap. Oymp. 76), 1977, 1969–182: Steryl glycosides and acylated steryl glycosides.

49. (a) H. Murai, K. Kitaguchi, T. Suminokura, A. Sano, M. Kise, M. Kitano and T. Tomita; U.S. Patent No. 3,991,186: Steryl-B-D-glucoside ester pharmaceutical compositions and method of use.
(b) H. Murai et al; Offenlegungsschrift No. 2533898: Verfahren zur Gewinnung von Steryl-B-D-glucoside-palmitaten. and Offenlegungsschrift No. 2533899: Verfahren zur Gewinnung von Steryl-B-D-glukosidestern.

50. S. Inoue, M. Kawamata, H. Ushimaru, K. Nakamidi and Y. Takahasi; Offenlegungsschrift No. 2615336: Verfahren zur gewinnen von leicht absorbierbarim Steringlykosid.

51. (a) S. Inoue, M. Kawamata, H. Ushimaru, K. Nakamidi and Y. Takahashi; British Pat. No. 1,489,532: Improvement in or relating to steryl glucoside palmitates.
(b) S. Inoue et al; Offenlegungsschrift No. 2621222: Verfahren zur Gewinnen von leicht absorbierbaren amorphen sterylglukosidepalmitatem und ihren zubereifungen.

52. (a) K. Ohata, T. Nomura and M. Watanabe; British Pat. No. 1,491,549: Haemostatic, vascular stabilizers and anti-shcok agents and British Pat. No. 1,491,550: Pharmaceutical composition.
(b) K. Ohata et al; Offenlegungsschrift No. 2523284: H Haemostatische, gefäss stabilisierende und Antischeckmittel.

53. T. Murakami, N. Tanaka, T. Tezuka and C. M. Chen; Chem. Pharm. Bull, 1975, 23, 1634–1637: Chemische Untersuchungen der Inhaltstoffe von Pteris cnaequalis Baker var aequata (M.Q) Tagawa.

54. S. A. Rizoi, J. Lal and P. C. Gupta; Phytochemistry, 1971, 10, 70–71: Examination of a phytosterolin from a Cassia plant.

55. O. C. Dass Gupta, S. A. I. Rizoi and P. C. Gupta, Planta Melica, 1971, 20, 172–177, Chemical examination of a phytosterolin from the seeds of Ipomea fistulosa.

56. G. Misra, S. K. Nigam and C. R. Mitra, Acta. Phytotherapeutic, 1971, 18, 134–136; Chemical examination of abolmoschus moschatus leaf, flower and fruit.

57. N. Weber; Chem. Phys. Lipids, 1977, 18, 145–148: Eine einfache Synkese acetzlierter steryl B-glykoside.

| Name | Preparative Molar reagent ratios: Anhydride/ sterolin | m.p. °C. | Spec. rot. $[\alpha]_D^{25}$ | solvent | Formula Composition | Mol. Mass | Analysis % calc. C | Analysis % calc. H | Analysis % found C | Analysis % found H | Solubility g/l |
|---|---|---|---|---|---|---|---|---|---|---|---|
| sitosteryl β-D-glucoside | (S.G.) | 297–301 | | | $C_{35}H_{60}O_6$ | 576 | 72,9 | 10,4 | | | $9 \times 10^{-3}$ |
| stigmasteryl β-D-glucoside | (St.G.) | | | | | | | | | | |
| ergosteryl β-D-glucoside | (E.G.) | | | | | | | | | | |
| cholesteryl β-D-glucoside | (C.G.) | | | | | | | | | | |
| 5α-cholestanyl β-D-glucoside | (Cta.G.) | | | | | | | | | | |
| sitosteryl β-D-galactoside | (S.Ga.) | | | | | | | | | | |
| lanosteryl β-D-glucoside | (L.G.) | | | | | | | | | | |
| 22,23-dihydrolanosteryl β-D-glucoside | (LH₂G.) | | | | | | | | | | |
| sitosteryl β-D-maltoside | (S.M.) | 215–289* | | | $C_{41}H_{70}O_{11}$ | 738 | 66,7 | 9,5 | | | $3.8 \times 10^{-1}$ |
| sitosteryl β-D-lactoside | (S.L.) | | | | | | | | | | |
| sitosteryl β-D-cellobioside | (S.C.) | | | | | | | | | | |
| S.G. 6'-O-β-D-maltoside | (S.T.) | 280–310* | | | $C_{47}H_{18}O_{16}$ | 900 | 62,7 | 8,9 | | | |
| S.G. monohemisuccinate+ | | 258* | | | $C_{39}H_{64}O_9$ | 676 | 69,2 | 9,5 | 68,05 | 9,3 | $6,5 \times 10^{-2}$ |
| S.G. dihemisuccinate | | 246* | | | $C_{43}H_{68}O_{12}$ | 776 | 66,5 | 8,8 | 65,2 | 9,2 | $1,25 \times 10^3$ colloidal |
| S.G. trihemisuccinate+ | | 251* | | | $C_{47}H_{22}O_{15}$ | 876 | 64,4 | 8,2 | 63,2 | 8,6 | |
| S.G. tetrahemisuccinate+ | | 248* | | | $C_{51}H_{76}O_{16}$ | 976 | 62,7 | 7,8 | 62,9 | 8,0 | |
| S.Ga. dihemisuccinate | | | | | | | | | | | |
| S.M. dihemisuccinate | | | | | | | | | | | |
| S.G. dihemiglutarate | | | | | | | | | | | |
| S.G. dihemimaleate | | | | | | | | | | | |
| S.G. dihemicyclohexanedicarboxylate | | | | | | | | | | | |
| S.G. dihemiphthalate | | | | | | | | | | | |
| St.G. dihemisuccinate | | | | | | | | | | | |
| E.G. dihemisuccinate | | | | | | | | | | | |
| C.G. dihemisuccinate | | | | | | | | | | | |
| Cta.G. dihemisuccinate | | | | | | | | | | | |
| L.G. dihemisuccinate | | | | | | | | | | | |
| LH₁G. dihemisuccinate | | | | | | | | | | | |
| L.G. trihemisuccinate | | | | | | | | | | | |
| S.G. monohemisuccinate | Na salt+ | 330 | | | $C_{39}H_{63}O_9Na$ | 698 | 67,0 | 6,0 | | | $8,5 \times 10^{-2}$ colloidal |
| S.G. dihemisuccinate | Na₂ salt | 320* | | | $C_{43}H_{66}O_{12}Na_2$ | 820 | 62,9 | 8,0 | 62,2 | 8,0 | $2 \times 10^3$ |
| S.G. dihemisuccinate | K₂ salt | 330+* | | | $C_{43}H_{66}O_{12}K_2$ | 852 | 60,6 | 7,7 | | | $2,5 \times 10$ |
| S.G. dihemisuccinate | (NH₄)₂ salt | 265* | | | $C_{43}H_{74}O_{12}N_2$ | 810 | 63,7 | 9,1 | 64,0 | 9,2 | |
| S.G. dihemisuccinate | Ca salt | 315* | | | $C_{43}H_{66}O_{12}Ca$ | 814 | 63,4 | 8,1 | 63,2 | 8,2 | insoluble |
| S.G. trihemisuccinate | Na₂H salt+ | | | | | | | | | | |
| S.G. trihemisuccinate | Na₃ salt+ | 320* | | | $C_{47}H_{69}O_{15}Na_3$ | 942 | 59,6 | 7,3 | 56,7 | 8,1 | $4-3 \times 10^4$ |
| S.G. tetrahemisuccinate | Na₄ salt+ | 320* | | | $C_{51}H_{72}O_{16}Na_4$ | 1064 | 57,5 | 6,8 | 53,1 | 7,2 | |
| S.Ga. dihemisuccinate | Na₂ salt | | | | | | | | | | |
| S.M. monohemisuccinate | Na salt | | | | | | | | | | |
| S.G. dihemiglutarate | Na₂ salt | | | | | | | | | | |
| S.G. dihemimaleate | Na₂ salt | | | | | | | | | | |
| S.G. dihemicyclohexandicarboxylate | Na₂ salt | | | | | | | | | | |
| S.G. dihemiphthalate | Na₂ salt | | | | | | | | | | |
| St.G. dihemisuccinate | Na₂ salt | | | | | | | | | | |
| E.G. dihemisuccinate | Na₂ salt | | | | | | | | | | |
| C.G. dihemisuccinate | Na₂ salt | | | | | | | | | | |
| Cta.G. dihemisuccinate | Na₂ salt | | | | | | | | | | |
| L.G. dihemisuccinate | Na₂ salt | | | | | | | | | | |
| LH₂.G. dihemisuccinate | Na₂ salt | | | | | | | | | | |
| L.G. trihemisuccinate | Na₂ salt | | | | | | | | | | |

*These melting points were not sharp. Melting took place over an extended temperature range with slight decomposition (browning). A clear melt was finally reached at the given temperature.

+The sitosterol used for the preparation of these compounds originated from soybeans. The approximate composition of this soysterol was 63% sitosterol, 32% campesterol and 5% stigmasterol. The sitosterol used for the preparation of all the other sitosterolins, their hemiesters and their salts originated from tall oil pitch and consisted approximately of 95% sitosterol with 5% of a mixture of dihydrositosterol and campesterol.

(a) Further products will be prepared during the next twelve months, existing data will be checked where necessary and missing information will be completed.

(b) In the final TABLE some of the compounds may be excluded while new ones may be added.

We claim:

1. A pharmaceutically-acceptable dicarboxylic acid hemiester of a steryl glycoside.

2. The compound according to claim 1 wherein the hemiester residue is derived from one of the group consisting of hemisuccinate, hemiglutarate, hemimaleate, hemicyclohexandicarboxylate and hemiphthalate.

3. The compound according to claim 1 or claim 2 consisting of the steryl glycoside from the group consisting of the glycosides of sitosterol, stigmasterol, ergosterol, cholesterol, 5a-cholestanol, lanosterol, 22,23- dihydrolanosterol, campasterol, cycloartenol and a-spinasterol.

4. An anti-inflammatory composition including a pharmaceutically-acceptable dicarboxylic acid hemiester of a steryl glycoside in a pharmaceutically-effective amount together with an inert carrier.

5. An anti-inflammatory composition according to claim 4 wherein the hemiester is chosen from the group consisting of the hemisuccinates, hemiglutarates, hemimaleates, hemicyclohexandicarboxylates and hemiphthalates of sitosterol, stigmasterol, ergosterol, cholesterol, 5a-cholestanol, lanosterol, 22,23-dihydrolanosterol, campasterol, cycloartenol and a-spinasterol glycosides.

6. The composition of claim 5 wherein the glycoside is a glucoside.

7. The composition of claim 6 wherein the hemiester is a hemisuccinate.

8. The compound of claim 3 wherein the glycoside is a glucoside.

9. The compound of claim 1 wherein the hemiester is a hemisuccinate of a steryl glucoside wherein the sterol is chosen from the group consisting of sitosterol, stigmasterol, erogsterol, cholesterol, 5a-cholestenol, lanosterol, 22,23-dihydrolanosterol, campasterol, cycloartenol and a-spinasterol.

10. The compound of claim 9 wherein the glucoside is the glucoside of sitosterol.

11. The compound of claim 1 wherein the hemiester is a hemisuccinate of a steryl glycoside which is a glucoside, galactoside or maltoside of a sterol group consisting of sitosterol, stigmasterol, ergosterol, cholesterol, 5a-cholestanol, lanosterol, 22,23-dihydrolanosterol, campasterol, cycloartenol and a-spinasterol.

12. The method of treating an inflammatory illness comprising administering to a mammal an anti-inflammatory amount of a compound of claim 1.

13. The method of claim 12 wherein the hemiester is selected from the group consisting of hemissuccinates, hemiglutarates, hemimaleates, hemicyclohexandicarboxylates and hemiphthalates of a steryl glycoside wherein the sterol is chosen from the group consisting of sitosterol, stigmasterol, ergosterol, cholesterol, 5a-cholestanol, lanosterol, 22,23-dihydrolanosterol, campasterol, cycloartenol and a-spinasterol.

14. The method of claim 13 wherein the glycoside is a glucoside, galactoside or maltoside.

15. The method of claim 14 wherein the glycoside is a glucoside.

16. The method of claim 15 wherein the hemiester is a hemisuccinate.

17. The method of claim 14 wherein the hemiester is a hemisuccinate.

18. The method of claim 13 wherein the hemiester is a hemisuccinate.

* * * * *